(12) United States Patent
Otto et al.

(10) Patent No.: US 8,747,464 B2
(45) Date of Patent: Jun. 10, 2014

(54) DEVICE AND SYSTEM FOR ASSISTING AND/OR TAKING OVER THE PUMPING FUNCTION OF THE HEART

(75) Inventors: Thomas Otto, Jena (DE); Andreas Klein, Jena (DE)

(73) Assignee: PPA Technologies GmbH, Jena (DE)

( * ) Notice: Subject to any disclaimer, the term of this patent is extended or adjusted under 35 U.S.C. 154(b) by 568 days.

(21) Appl. No.: 12/991,978

(22) PCT Filed: Apr. 14, 2009

(86) PCT No.: PCT/EP2009/002710
§ 371 (c)(1),
(2), (4) Date: Nov. 10, 2010

(87) PCT Pub. No.: WO2009/127384
PCT Pub. Date: Oct. 22, 2009

(65) Prior Publication Data
US 2011/0098806 A1    Apr. 28, 2011

(30) Foreign Application Priority Data

Apr. 14, 2008   (DE) .......................... 10 2008 018 919

(51) Int. Cl.
*A61M 1/10*    (2006.01)
(52) U.S. Cl.
USPC .......................................................... 623/3.1
(58) Field of Classification Search
USPC ....................................... 623/3.1; 600/16, 17
See application file for complete search history.

(56) References Cited

U.S. PATENT DOCUMENTS

| 5,707,336 A | 1/1998 | Rubin |
| 6,572,529 B2 | 6/2003 | Wilk |
| 2004/0102674 A1 | 5/2004 | Zadini et al. |
| 2007/0191672 A1 | 8/2007 | Ferrari |
| 2010/0152523 A1 | 6/2010 | MacDonald et al. |

FOREIGN PATENT DOCUMENTS

| DE | 199 51 220 A1 | 4/2001 |
| WO | 2005/110513 A1 | 11/2005 |
| WO | 2007/062239 A2 | 5/2007 |

*Primary Examiner* — Thomas J Sweet
*Assistant Examiner* — Matthew Schall
(74) *Attorney, Agent, or Firm* — Roberts Mlotkowski; Safran & Cole, P.C.; David S. Safran

(57) ABSTRACT

A device for assisting and/or taking over the pumping function of the heart, with a multilayer sheathing part configured for compressing the heart at least in certain sections, wherein the sheathing part has at least one stabilization layer for shaping the sheathing part and at least one inner extensible augmentation layer, and wherein at least one cavity is formed between the stabilization layer and the augmentation layer, the cavity being inflatable and deflatable by a fluid, for cyclic compression of the heart. Provision is made for the stabilization layer to be inflatable with a fluid, at least in certain sections, in order to convert the sheathing part from a coiled and/or collapsed insertion state of the device in the body into an arched functional state, wherein the heart, in the functional state of the sheathing part, is at least partially sheathed and/or encompassed.

25 Claims, 19 Drawing Sheets

DEVICE AND SYSTEM FOR ASSISTING AND/OR TAKING OVER THE PUMPING FUNCTION OF THE HEART

BACKGROUND OF THE INVENTION

1. Field of the Invention

This invention relates to a device for assisting and/or taking over the pumping function of the heart, comprising a multi-layer sheathing part configured for compressing the heart at least in certain sections, wherein the sheathing part has at least one stabilization layer for shaping the sheathing part, and at least one inner extensible augmentation layer, and wherein between the stabilization layer and the augmentation layer at least one cavity is formed, which is inflatable and deflatable by means of a fluid, for cyclic compression of the heart.

2. Description of Related Art

A device for pericardially assisting and/or taking over the cardiac activity of the above-mentioned type is known, for instance, from the German Patent Application DE 199 51 220 A1. This is a not very invasive, i.e., percutaneously implantable system, for mechanically assisting and temporarily replacing the pumping function of the heart. After probing of the pericardium, the device is inserted percutaneously into the pericardium, or at the end of an operation is surgically positioned inside the pericardium, and placed therein with a double membrane around the right and left ventricle. In a deflated state of the double membrane, the device is so thin that compression of neighboring organs is avoided. After implantation, the cavity of the double membrane is rhythmically loaded via a connecting tube with a fluid, which may be a gas (helium or $CO_2$) or some appropriate liquid. Due to this rhythmical inflating and deflating of the cavity of the double membrane, and because the outer membrane, in contrast to the inner membrane, is not extensible, pressure transmission and compression of the heart via the double membrane enclosing the heart occurs. In doing so, blood from the right ventricle is expelled into the pulmonary artery, and simultaneously, from the left ventricle into the aorta, or if a pumping function of the heart is present, the systolic ejection work of the cardiac muscle is assisted.

A similar device—albeit operating epicardially—is known from the International Patent Application Publication WO 2005/110513 A1. This device also provides a double membrane for epicardially assisting and/or taking over cardiac activity, having an elastic inner membrane and a non-elastic outer membrane, as well as a closed cavity formed therebetween, which is inflatable and deflatable by means of a fluid, with a first chamber assigned to the right ventricle and a second chamber assigned to the left ventricle. The first chamber and the second chamber are connected together via at least one valve inside a dividing wall separating both chambers. As required, double membranes can be manufactured, which allow for the sole augmentation of the right ventricle, or—in another embodiment—of the left ventricle only, both while maintaining the possibility of assisting both ventricles simultaneously.

The devices described above are fastened directly to the heart and to the organs surrounding the heart inside the thorax, so that the devices are constantly in direct contact with the heart surface. However, mounting and fixing the devices to the delicate tissue of the heart, lungs, and great vessels is only possible in a limited way because of the organs' macro and micro-anatomical nature. Frictional forces occurring between the device and tissue can at very short term, within hours and days, lead to considerable irreparable tissue damage; penetrations of the ventricles and great vessels inside the thorax will result in the patient's death within minutes. Also, when mounting and fixing the devices directly to the heart, the intrinsic heart action may be hindered or affected, with the heart, due to the mechanical pumping function thereof, exhibiting cyclic shortening or lengthening of the heart axis with simultaneous spiral-like rotation about the heart axis. Another challenge for devices to be introduced inside the thorax is due to the spatial and positional relations between organs (heart, lung, great vessels) on the one hand, as well as between thoracic organs and the inner wall of the thorax on the other hand. They offer very limited possibilities for deploying instruments or devices introduced into the thorax at or around the heart or for bypassing the heart.

SUMMARY OF THE INVENTION

It is an object of the present invention to provide a device and a system, respectively of the type mentioned at the beginning, which in case of need allow for direct cardiac massage or directional cyclic compression and decompression of the heart, whereby the mechanical pumping function of the heart may be assisted or replaced. Besides, the device is to be easily introduced and removed into and out of the thorax in a minimally invasive way, i.e., without conventional surgical opening of the thorax (thoracotomy). Moreover, the structure and operating mode of the device are to allow for positionally true positioning within the thorax at or around the heart, without the risk of damage to the heart and/or surrounding organs. In operating state, i.e., when cyclically compressing and decompressing the heart, mobility of the beating heart must not be impaired, or only to a negligible extent. Finally, it must be possible for the device and system to be manufactured in a cost-effective way.

In a device of the type mentioned at the beginning, the above-mentioned objects are achieved in that the stabilization layer is inflatable in certain sections by means of a fluid and deflatable by discharging the fluid, so as to convert the sheathing part through inflation of the stabilization layer from a coiled and/or collapsed insertion state during insertion of the device into the body into a curved functional state, wherein the heart in the functional state of the sheathing part is at least partially sheathed and/or encompassed by the sheathing part. Preferably, in the functional state, the stabilization layer substantially completely encases or encompasses both ventricles of the heart. In addition to the device, the inventive system has at least one auxiliary device for allowing for minimally invasive introduction of the inventive device into the body.

The invention is based on the fundamental idea of providing a device for assisting and/or taking over the pumping function of the heart, which can be deployed inside the thorax. Thereby, the inventive device may be applied in a surgically not very invasive and not very complicated way, and allows for readily available adequate assistance of the pumping function of the heart, in particular in emergency situations, e.g., in case of acute heart failure with cardiac output of less than 50% up to complete loss of the mechanical cardiac function. In the inventive device, the sheathing part may be uncoiled or unfolded via the inflatable and deflatable stabilization layer, with the heart and/or the heart inside the pericardium (pericard) being sheathed, encompassed, or enclosed by the sheathing part in the functional state. In this respect, the stabilization layer is meant for ensuring sufficient rigidity or stability of the device implanted at or around the heart, as well as for conforming to the shape of the heart. As the sheathing part can be collapsed or coiled up flexibly, a minimally invasive introduction of the device into the thorax and later removal without conventional surgical opening of the thorax is possible. The stabilization layer is provided for unfolding or uncoiling of the sheathing part and configured accordingly.

The augmentation layer has significantly greater extensibility than the stabilization layer. If a gas or gaseous mixture is cyclically fed into the cavity between the stabilization layer and the augmentation layer, with correspondingly existing overpressure inside the cavity, inwardly directed bulging of the cavity is caused, which is meant for compression of the neighboring ventricles, as well as for cardiac massage and assistance of the cardiac function. It should be appreciated that alternatively also the augmentation layer as such may be inflatable.

Preferably, in the functional state, the sheathing part has a flare-like tulip shape adapted to the shape of the heart, with the heart, in the functional state of the sheathing part, being sheathed and/or encompassed from front to back over the lateral walls and, preferably, over the apex of the heart up to the region of the posterior walls of the heart. It should be appreciated that the stabilizing layer must be configured accordingly in order to ensure the conformation of the sheathing part by inflating or uncoiling and/or deploying during conversion from the insertion state into the functional state. Relating to the functional state, the augmentation layer may be provided only in the region above the lateral walls of the heart and the posterior walls of the ventricles, so as to form the cavity for cyclically compressing and decompressing the heart in the region of the lateral walls and the posterior walls of the heart. In another embodiment of the invention, it may also be provided for the inventive device to expose the apex of the heart or not to sheathe or encompass it.

The rigidity of the sheathing part, which is required for assisting and/or taking over the pumping function of the heart, is produced by feeding a gas or an appropriate liquid into inflatable regions of the stabilization layer. In this respect, the sheathing part in the insertion state may comprise an inflatable edge portion, which is spirally coiled and/or folded from outside to inside. By feeding a gas or an appropriate liquid into the stabilization layer the edge region of the sheathing part may be uncoiled or deployed accordingly so as to obtain the conformation of the sheathing part to the shape of the heart. Preferably, the sheathing part may be coiled or folded up starting from both longitudinal edges towards the middle of the sheathing part, so that the sheathing part can be coiled up or collapsed into a very small insertion size in the insertion state, thereby simplifying the minimally invasive introduction into the thoracic cavity and the later removal from the thoracic cavity without conventional surgical opening of the thorax.

So as not to damage or injure the great heart vessels with the inventive device when assisting and/or taking over the pumping function of the heart, it is provided, preferably, for the sheathing part, in the functional state, to have a preferably hyperbolic recess open towards the top for the great heart vessels on the backside, i.e., on the side facing the posterior walls of the heart.

Moreover, the inventive device comprises means enabling reversible fastening or fixation of the implanted device inside the thoracic cavity without the device being fastened at the heart as such or at the pericardium, lungs, or great vessels inside the thoracic cavity. For this purpose, at least one fastening means for heart and/or pericardium-free fastening of the sheathing part is provided, preferably for fastening to an inner wall of the thorax and/or to at least one rib of the patient. As a fastening means, preferably, a plurality of suction cups for suction on the inner wall of the thorax may be provided, so that the device may be fastened positionally true to the inner wall of the thorax above the heart. Due to heart and pericardium-free fastening of the sheathing part or the inventive device the mobility of the beating heart is not hindered in spite of assistance to the pumping function.

Alternatively, fastening may also be implemented in the space between the ribs, by being supported through clamping or expansion at the surrounding ribs, or via two mutually screwed plates inside and outside the thorax. Also, fastening at the breastbone and/or coastal arch by clamping, wedging, screw fitting or stitching is possible. Moreover, percutaneous fastening may be provided, wherein the inventive device may have a distal end, which is fastened in the skin, e.g., by stitching, gluing, or clamping. Finally, fastening may be done via micro-hooks or adhesive members located on the device or by reversible gluing to the inner thoracic wall. Furthermore, fastening at the thoracic diaphragm is possible, wherein the inventive device may be supported with its distal end on this muscle plate and fastened by stitching, clamping, or hooking.

If a plurality of suction cups is provided as a fastening means, then they are connected to at least one fluid line for aspirating or discharging the aspiration spaces created between the suction cups and an inner wall of the thorax. Aspiration allows for the pressure in the aspiration spaces to be reduced, and thus for positionally true fastening of the inventive device above the heart at the inner wall of the thorax. Moreover, lubricating liquid may be supplied via the suction cups in order to obtain improved sliding properties.

In a particularly preferred embodiment of the inventive device, on the front of the sheathing part in the region of the medial longitudinal axis, a non-inflatable base part connected to the sheathing part is provided, with the base part comprising the fastening means and, wherein preferably, the base part with respect to the arrangement in the functional state is extending in parallel to the heart axis from an upper edge of the sheathing part over the heart base to the bottom towards the apex of the heart. The base part is provided for fastening the device inside the thoracic cavity or for holding the sheathing part. Base part and sheathing part are preferably different components of different layer structure and/or different rigidity, which are solidly interconnected. Preferably, the base part comprises as a holding member a plurality of suction cups, which are superficially arranged over the base part. Furthermore, at the base part, micro-hooks or adhesive members may be provided in order to fasten the inventive device to the inner thoracic wall. Between the sheathing part and the base part, a complete connection, existing over the full length of the base part, may be provided. This connection between both parts is mainly meant for fixing the sheathing part via the base part at the inner wall of the thorax. In this case, the base part may rest with the full length thereof on the sheathing part, the connection between both parts being provided on the whole underside or at least part of the underside of the base part. Herein, the underside is supposed to be the side of the base part facing the heart. Basically, it is of course also possible for the base part to be only partially connected to the sheathing part, i.e., in certain sections over the length thereof.

Besides, the base part may comprise at least one outer application layer configured for applying a lubricating liquid on the inner and/or outer side of the base part, with an inner channel system and pore-like orifices toward the inner side and/or outer side. It will be understood that the inner channel system is accordingly connected to at least one fluid line so as to discharge a lubricating liquid over the application layer. Discharging a lubricating liquid allows for possible frictional forces and tissue damage to be reduced. If the base part on the inner side thereof is applied directly to the surface of the heart, then discharging a lubricating liquid on the inner side may allow for the surface of the heart and the inner surface of the inventive device to slide on each other with minimal frictional forces occurring.

The base part may have an elongated shape, with the length of the base part being preferably about ⅔ of the length of the front side of the sheathing part relating to the functional state. Thereby fastening of the base part to the inner thoracic wall is simplified.

Besides, the base part is preferably configured elastically so that the base part adapts to the bulge of the inner wall when being fastened to the inner wall of the thorax. Thereby, secure fastening of the base part is simplified, whereby for instance the suction cups provided for fastening of the base part to the inner wall may adhere to the inner wall on the whole surface.

In order to ensure the conformation of the sheathing part, required for cardiac assistance, during conversion from the insertion state into the functional state on the one hand, and as small a size as possible for the inventive device in the insertion state on the other hand, in a preferred embodiment, the base part in relation to the arrangement in the functional state is only connected to the sheathing part in the region between the upper edge of the sheathing part and the base of the heart. Thereby, the conformation of the sheathing part is not hindered by the fastening to the base part, but at the same time, secure holding of the sheathing part is ensured.

In order to achieve the conformation of the sheathing part to the heart during conversion from the insertion into the functional state, it is advantageous for the sheathing part in relation to the insertion state to have two coiled and/or folded inflatable edge portions extending in the longitudinal direction, with the base part being arranged between the edge portions, and with both edge portions converging into a common round-bottom-shaped edge portion for sheathing and/or encompassing the apex of the heart. Each coiled and/or folded edge portion extending in the longitudinal direction may in relation to the insertion state comprise a straight fastening portion for fastening to the base part, and a free portion following the straight fastening portion, curving away from the plane of the base part, and not being fastened to the base part, whereby the free portions arranged on both longitudinal sides of the base part converge at the round-bottom-shaped edge portion. Moreover, in relation to the insertion state, the free portions are preferably articulated outwards and/or curved away from the plane of the base part with respect to the straight fastening portions. Between the straight fastening portions, a recess for receiving and fastening the base part may be formed, thereby allowing for secure fastening of the base part to the sheathing part on the one hand, and a small size in the insertion state as well as the required conformation of the sheathing part, on the other hand.

The stabilization layer may have a honeycomb structure with a plurality of adjacent honeycomb cells, with the honeycomb cells being connected to at least one fluid line for cyclically supplying a fluid into the honeycomb cells, with the honeycomb cells preferably having a cross-section tapering towards the heart with a larger base area on the side remote from the heart, and with a smaller base area on the side close to the heart, and wherein, if a fluid is supplied into the honeycomb cells, the honeycomb cells inflate, and an inward arching of the sheathing part is caused. The stabilization layer has a honeycomb-like structure and is not very or not at all extensible. When a compressed gas or gaseous mixture is filled into the honeycomb structure, a higher gas pressure is generated within the honeycomb cells. This higher gas pressure provides the inventive device implanted inside the thorax with the necessary shape (curvature) for sheathing or encompassing or encircling the heart. At the same time, the overpressure within the honeycomb cells will provide the inventive device with the necessary rigidity, which is required for assisting or taking over the pumping function of the heart.

Preferably, the sheathing part comprises a stabilization layer with a corresponding honeycomb structure, which will lead to a simple constructive architecture of the inventive device and low manufacturing cost. In principle however, it is also possible to provide several stabilization layers with honeycomb-like cells, with the layers overlapping completely or only partially, and possibly having a structure like a roof tile assembly. The stabilization layer preferably extends over the whole area of the sheathing part. In principle however, it is also possible for the stabilization layer to extend over the area of the sheathing part in certain sections only. In this respect, the sheathing part in the functional state may also encompass or grip the heart in a finger-like fashion only.

In another embodiment of the invention, at least one stabilization wire may be provided for the sheathing part, with the stabilization wire being arranged preferably between the stabilization layer and the augmentation layer. In particular, a stabilization wire starting from the base part of the device and placed at the posterior pole of the encompassing of the sheathing part around the apex of the heart may be provided, which may be provided as an additional stabilization support for the sheathing part and as an assisting member during the introduction of the inventive device into the body. The stabilization wire may allow for the lower region of the sheathing part to be pulled around the apex of the heart when the device is inserted. Thereby, a minimally invasive introduction of the inventive device into the body is simplified.

In addition to the stabilization layer, at least one service layer connected with the stabilization layer for supplying a fluid into the honeycomb cells may be provided. Preferably, servicing of the honeycomb cells with the fluid is done via three service or fluid lines separated from each other, whereby three neighboring honeycomb cells can be filled with fluid through different service performances. This ensures that even in case of leakage inside a honeycomb cell, no pressure loss may occur in a neighboring honeycomb cell, so that the rigidity and stability of the sheathing part is maintained even in case of leakage.

Just like the base part, the sheathing part may comprise at least one application layer configured for applying a lubricating liquid on the inner and/or outer side of the sheathing part, with an inner channel system and pore-like orifices towards the inner side and/or outer side of the functional part. The lubricating liquid reduces frictional forces between the inner surface of the sheathing part facing the surface of the heart and the surface of the heart during cyclic compression of the heart. In this respect, preferably a shifting gap between the surface of the heart and the inner surface of the inventive device is to be created, wherein inside this shifting gap or space for extracorporeal liquids, gels and/or drugs and/or other substances may be applied. Preferably, the application of a lubricating liquid on the inner side and on the outer side of the sheathing part on the one hand, and of the base part on the other hand, is provided, so that a direct contact fit between the inner surface of the inventive device and the heart, or the heart inside the pericardium, as well as the outer surface of the inventive device and the adjacent lungs is avoided. Through pore-like orifices on the inner surface and/or outer surface of the device, liquids or gels may be delivered continuously or temporarily in order to reduce frictional forces. Depending on the thickness of the applied liquid or gel film, a direct contact fit between the inner surface of the inventive device with the heart and the outer surface of the device with the adjacent lung tissue may be completely prevented.

The application layer preferably extends over the whole surface of the sheathing part. As a result, the sheathing part in the inventive device is formed by a stabilization layer, which is preferably fitted on both sides with an application layer, wherein in the region above the lateral walls of the heart and the posterior walls of the ventricles (relating to the functional state of the sheathing part), between the stabilization layer and the application layer, the augmentation layer is provided, so that in this region the cavity for cyclic compression of the heart may be configured.

At the inner surface of the sheathing part and/or the base part, one or more electrodes may be mounted in order to integrate a pace-maker function into the device, or with at least two electrodes, to produce direct potentials for reproducing an ECG. If at least three electrodes are integrated into the device and spatially arranged, then three-dimensional ECG leads may be performed thereby.

Hereafter, minimally invasive introduction and removal of the inventive device will be explained.

1. Imaging

Imaging methods during the complete operation of insertion, such as, for instance, an X-ray image of the thorax, provide the treating physician with information on shapes, positional relations, and size of the organs inside the thoracic cavity before the introduction of the device, as well as during the insertion of the inventive device on the position of the auxiliary means introduced and the device within the body at the heart.

2. Selecting the Implemented Embodiment of the Device According to Shape and Size By inspecting the given thorax image and using the acquired insights, the treating physician selects which embodiment and size may be implemented for the particular patient. In view of the determined shape of the heart, he or she may then preferably make use of 4 basic forms of the device, which may comprise a selection of several secondary variants with different sized versions (small, medium, large, very large). The basic forms are:

Normal type—no noticeable changes in form with respect to the normal shape of the heart (conical cylinder) can be detected;

Left-hand type—noticeable enlargement of the left ventricle (e.g., in case of long-lasting chronic hypertension);

Right-hand type—noticeable enlargement of the right ventricle (e.g., in case of long-standing chronic lung diseases);

Round type—enlargement of the whole heart or very detailed heart.

3. Transcutaneous Insertion Channel through the Skin of the Upper Abdomen

After disinfection of the skin of the upper abdomen, an access to the region under the xiphoid process (Processus xiphoideus) of the breast bone to the abdominal cavity is created through a small cut (3-5 cm).

4. Probing of the Heart

Through the access created to the upper abdomen a spatula-like probing device, which is part of the inventive system, may be advanced in the direction of the thoracic cavity up to the heart. Herein, the thoracic diaphragm (diaphragma) is usually traversed via an anatomically existing gap (Larrey's cleft) to reach the thoracic cavity. Larrey's cleft is located in the front area of the thoracic diaphragm. After traversing the thoracic diaphragm, the spatula-like probing device is generally pivoted to the right (as seen by the inserting physician to the right into the left thoracic cavity side considering anatomical sides) in order to reach the apex of the heart.

5. Bypassing the Anterior Wall of the Heart

When the heart is reached and probed, the spatula-like probing device is carefully pushed between the anterior wall of the heart and the inner thoracic wall. Possible adhesions of the pericardium and the inner thoracic wall may be detached bluntly with the spatula-liken probing device. After the anterior wall of the heart has been bypassed and possible adhesions have been bluntly detached, the probing device is removed from the body by withdrawal.

6. Introducing the Inventive Device

A tube-like insertion device, which is also part of the inventive system, is introduced through the access in the upper abdomen by the proximal end, and advanced up to the apex of the heart. Next, a mobile positioning device forming another part of the inventive system, with the inventive device being fastened at the proximal end, is advanced through an insertion channel of the tube-like insertion device until the apex of the heart is reached. Now, the insertion device is pulled back by several centimeters, so that a mobile joint protrudes at the proximal end of the positioning device into the thoracic cavity from the proximal end of the insertion device. By further advancing, and due the mobility of the joint at the proximal end of the positioning device, it is now possible to position the inventive device in front of the heart in the direction of the heart axis. Fluid inlet and outlet lines of the inventive device are connected to a fluid service and control device arranged outside of the body. Afterwards, the sheathing part is deployed around the heart by means of gas pressure, and the device is fixed to the inner thoracic wall by means of the suction inside the base part of the device. The mobile positioning device is removed from the body through the insertion channel of the insertion device. The tube-like insertion device is pulled out the body via the inlet and outlet lines, and may be split into two half-shells outside of the body and thus removed from the inlet and outlet lines of the inventive device.

7. Applying Liquids, Liquid Mixtures, or Gels

After introduction, positioning, and reversible fastening of the inventive device to the inner thoracic wall, a liquid or liquid mixture or gel is applied to the inner and outer surface of the device through the respective application layer of the sheathing part. The wetting liquid film is supposed to create a shifting gap respectively between the inner surface of the device and the heart as well as the outer surface and the adjacent lungs in order to reduce frictional forces as far as possible.

8. Cyclic Pumping of the Augmentation Layer

Cyclic pumping with a gas or gas mixture in the augmentation layer of the sheathing part may allow for direct assistance of the pumping function of the heart.

The minimally invasive removal of the inventive device from the body includes the following process steps:

1. Evacuating Gases and Gas Mixtures

From all layers of the sheathing part gases and/or gas mixtures are evacuated, which will lead to deflation of the stabilization layer.

2. Releasing Fixation to the Inner Thoracic Wall

Suction in the region of the base part for fastening the device to the inner thoracic wall is ceased.

3. Withdrawing the Collapsible Device

As the sheathing part is made from collapsible and coilable materials, after step 1 and 2 of the operation of removal, the inventive device can be removed from the body, just like removing drainage from a body cavity, by pulling at the inlet or outlet lines.

4. Suturing the Skin

The passage point into the inside of the body at the upper abdomen is sutured after removal of the device.

Hereafter, sample embodiments of the invention will be explained in further detail with reference to the accompanying drawings.

DETAILED DESCRIPTION OF THE INVENTION

Figure 1:
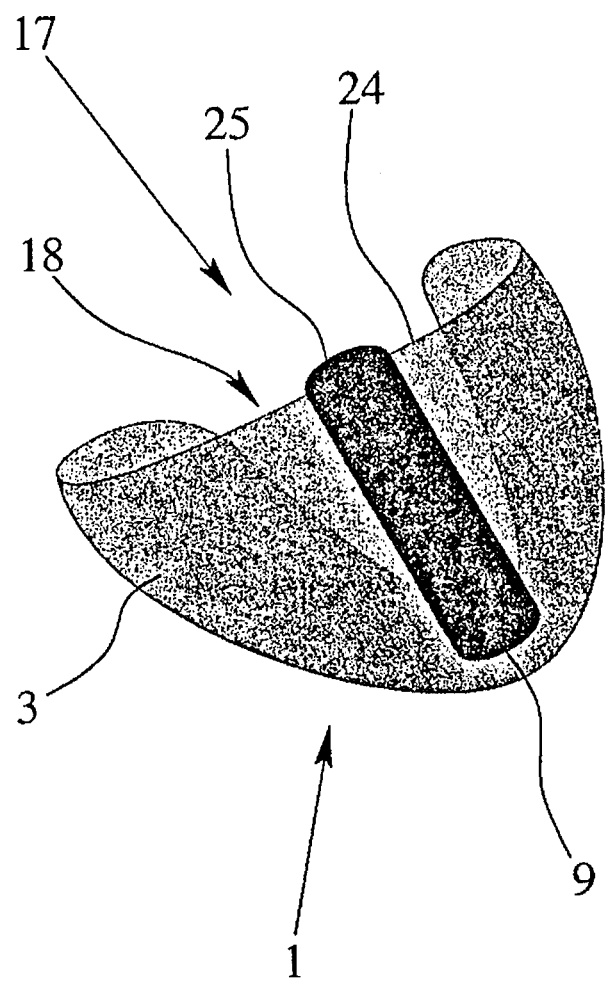
FIG. 1 shows a perspective representation of an inventive device for assisting and/or taking over the pumping function of the heart in the functional state of a sheathing part of the device.

In FIG. 1 a device 1 for assisting and/or taking over the pumping function of a heart 2 (shown FIGS. 2 and 3) which has a multilayer sheathing part 3, the sheathing part 3 being configured for compressing the heart, and the sheathing part 3 comprising a stabilization layer 4 (represented in FIGS. 7, 8, and 12) for shaping the sheathing part 3. Moreover, the sheathing part 3 comprises an inner extensible augmentation layer 5, (represented in FIGS. 7 and 8). At least one cavity 6 (represented in the inflated state in FIG. 7) is formed between the stabilization layer 4 and the augmentation layer 5, cavity 6 being inflatable by means of a fluid and then deflated for cyclic compression of the heart 2.

The stabilization layer 4 is inflatable by means of a fluid, at least in certain sections, in order to convert the sheathing part 3 from a coiled and/or collapsed insertion state of the device 1 (represented for instance in FIG. 4) that allows for insertion of the device 1 into the body, into an arched functional state (represented in FIG. 1). In the functional state, the heart 2 is at least partially sheathed and/or encompassed by the sheathing part 3.

Figure 2:
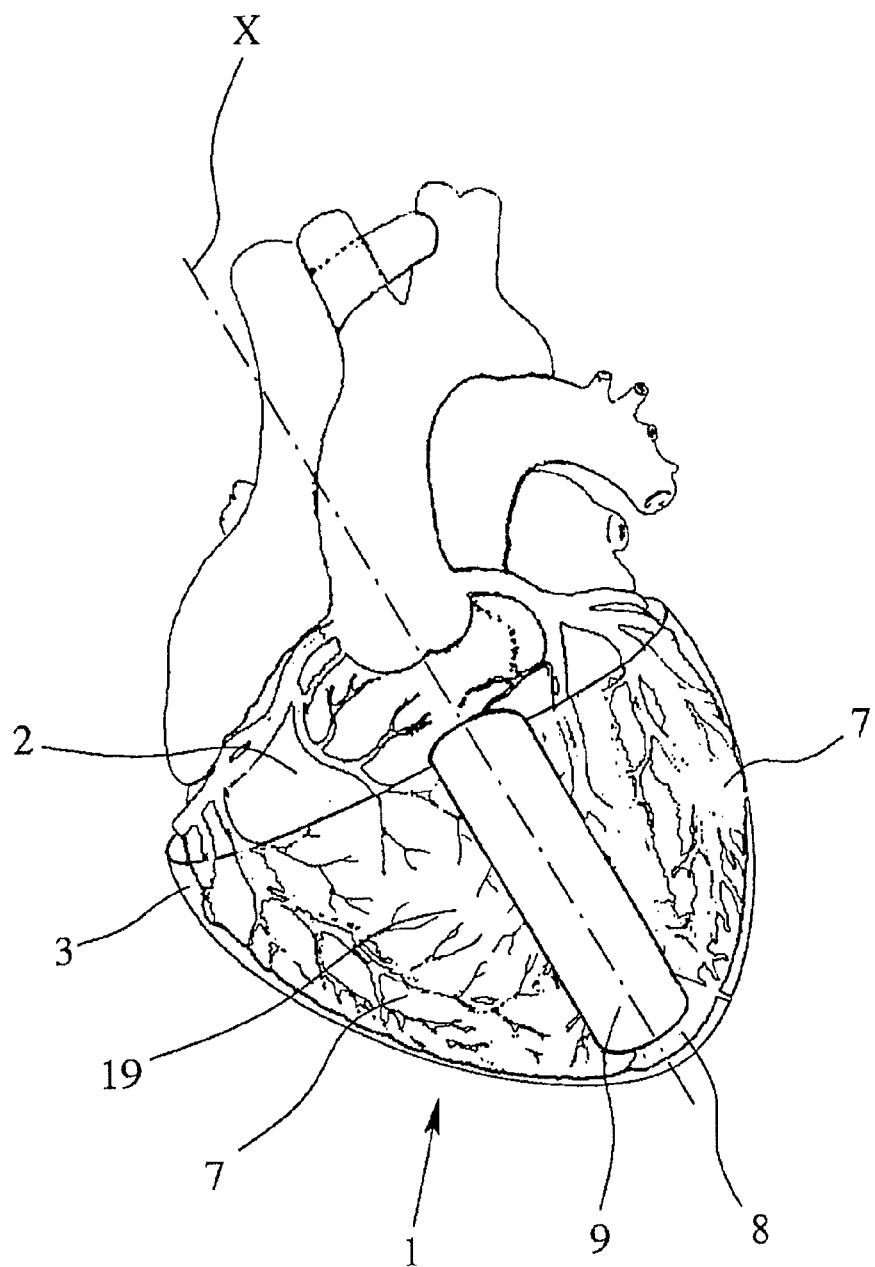
FIG. 2 shows the device represented in FIG. 1 in the functional state during cyclic compression and decompression of the heart in a front view.
Figure 3:
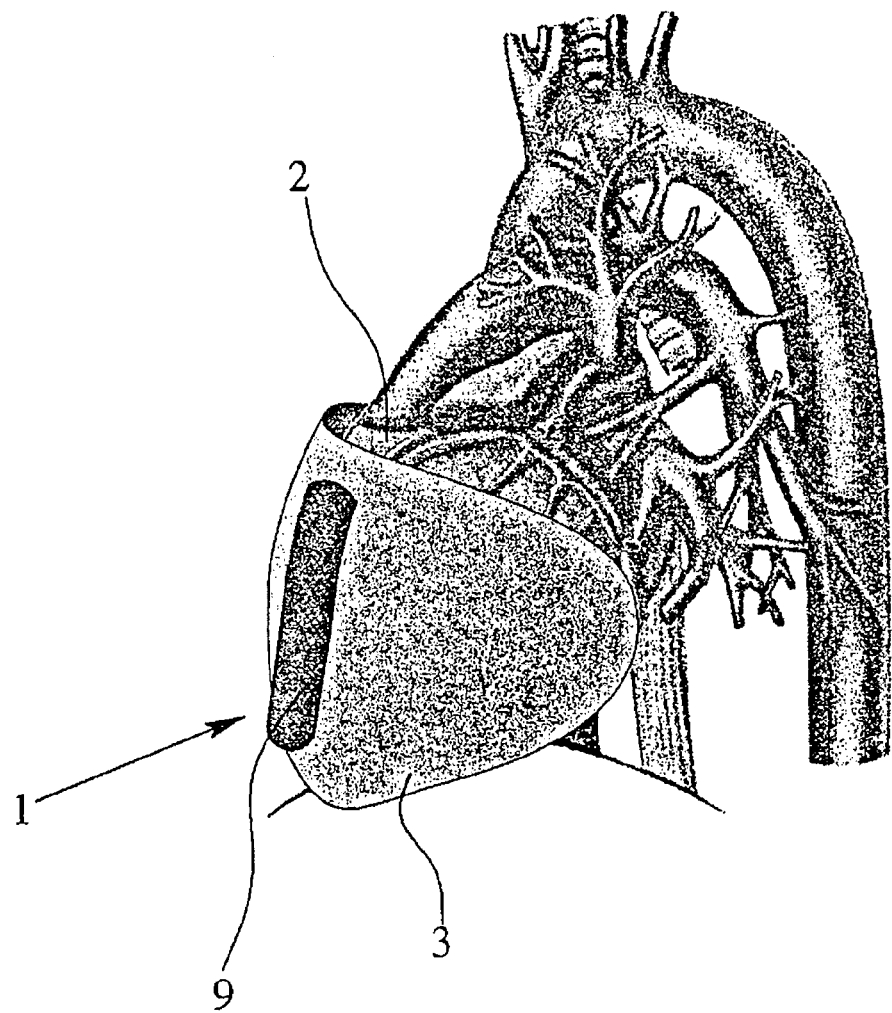
FIG. 3 shows the device represented in FIG. 1 in the functional state during cyclic compression and decompression of the heart in a lateral view.

In FIGS. 2 and 3, after minimally invasive introduction into the thoracic cavity of a patient, the device 1 is represented in the state of cyclic compression of the heart 1 from the front (FIG. 2) and from the side (FIG. 3). As can be seen from FIGS. 2 and 3, the sheathing part 3 of the device 1, in the functional state, has a flare-like tulip shape adapted to the shape of the heart 2, so that the heart 2 is sheathed from front to back over the lateral walls 7 of the heart 2 and over the apex of the heart 8 up to the region of the posterior walls of the heart 2 in the functional state of the sheathing part 3.

In addition to the sheathing part 3, the device 1 comprises a base part 9. The base part 9 is configured for fastening the device 1 to the thorax, and is situated towards the heart axis X in front of the heart 2 in the functional state represented in FIG. 2. The sheathing of the heart 2 is then obtained mostly by the sheathing part 3, starting from the sides as well as starting from the lower edge of the base part 9, over the sides of the heart 2 and around the apex of the heart 8. A suction device (not represented in FIGS. 1 to 3) at the base part 9 ensures fastening of the device 1 to the thorax. This allows for fixation of the device 1 without fastening to the heart, pericardium, lungs, or one of the great vessels inside the thorax.

The sheathing part 3 has a multilayer structure, which will be discussed later more in detail with reference to FIGS. 7 and 8 as well as 12 and 13. The rigidity of the implanted device 1 fastened to the thorax is produced by a compressed gas or gaseous mixture in one or more honeycomb-like structured layers of the sheathing part 3. Inside the sheathing part 3, preferably in the area above the lateral walls 7 and the posterior walls of the heart 2, one or more extensible layers are provided. If a gas or gaseous mixture is introduced cyclically into these extensible layers, and overpressure is produced, cyclic pre-arching of these layers and cyclic compression of the ventricles or assisting the cardiac function occurs.

Figure 4:
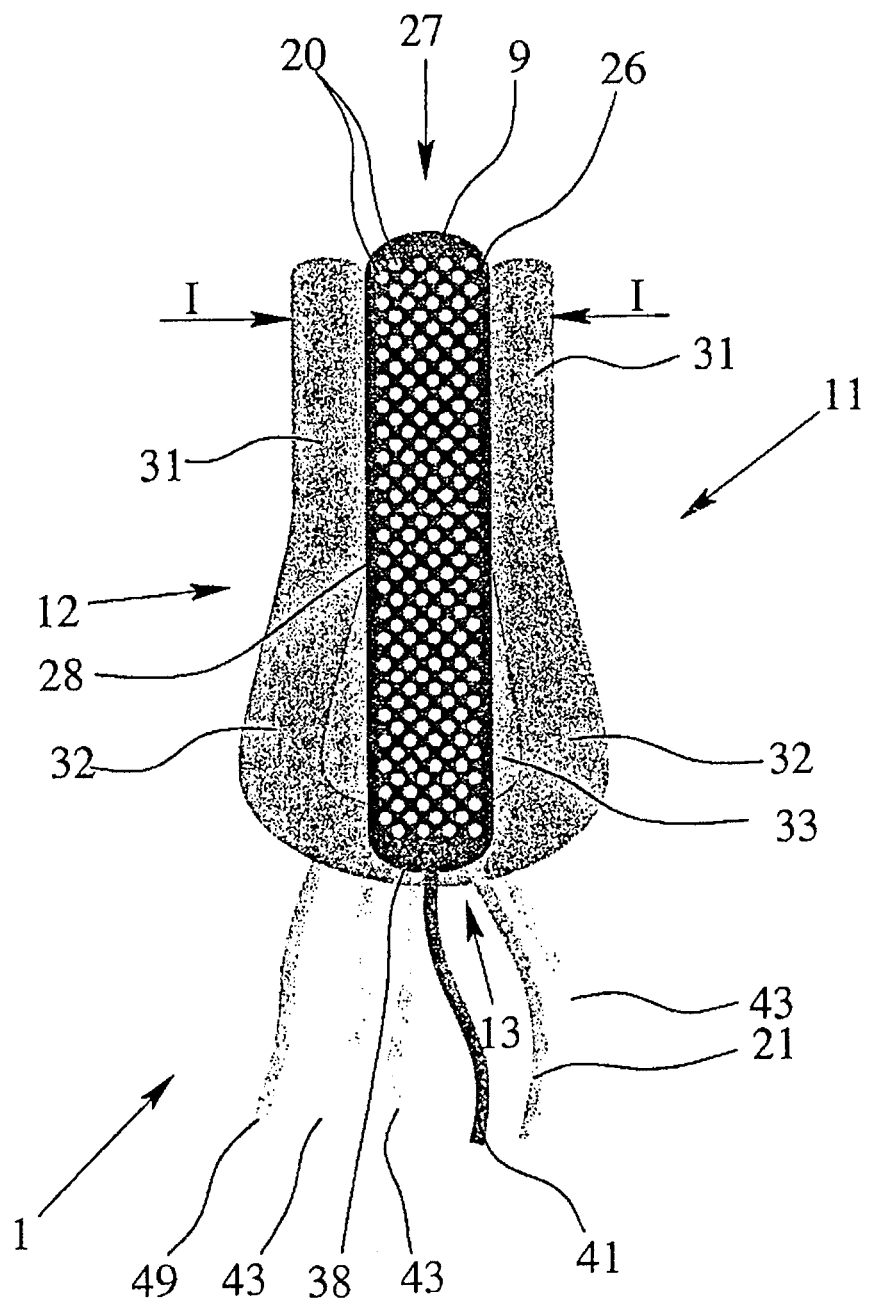
FIG. 4 shows the device represented in FIG. 1 in the collapsed insertion state in a top view.
Figure 5:
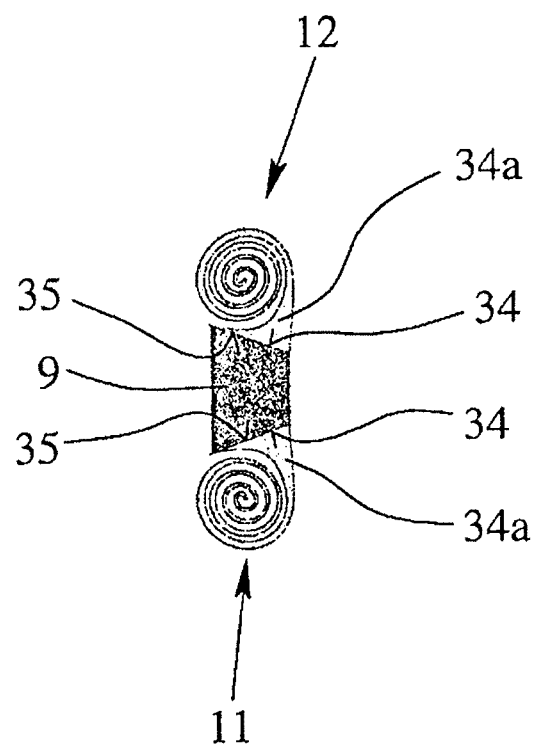
FIG. 5 a cross-sectional view of the inventive device taken along line I-I in FIG. 4.

As is apparent in particular from FIGS. 4 and 5, in relation to the insertion state, the sheathing part 3 comprises two spirally coiled and/or possibly collapsed edge portions 11, 12 extending in the longitudinal direction from outside to inside, with the base part 9 being arranged between the edge portions 11, 12, and with both edge portions 11, 12 converging into a common lower round-bottom-shaped edge portion 13, with respect to the functional state of the device 1 facing the apex of the heart 8, for sheathing and/or encompassing the apex of the heart. The edge portions 11, 12, 13 can be brought into an inflated state by means of a fluid, so that the sheathing part 3 adopts its shape adapted to the heart 2 and shown in FIGS. 2 and 3.

In the functional state, the sheathing part 3 forms on the backside 17 of the device 1 a preferably hyperbolical recess 18 open towards the top so that the sheathing part 3 may encircle the heart 2 without hindering the great heart vessels on the backside 17 of the heart 2.

On the side turned away from the heart 2 and towards the thorax, the base part 9 comprises superficially arranged suction cups 20. The suction cups 20 communicate via at least an inlet line with the extracorporeal space outside the body, whereby the inlet line 21 may create suction by which the device 1 is aspirated and fixed to the thorax. Of course, at the same time, the inlet line 21 allows for the suction to be released again. The inlet line 21 is preferably configured to be pressure or vacuum resistant, gas and liquid-tight. Besides, the inlet line 21 allows for a liquid to be introduced in support, whereby better sliding properties are warranted at the same time.

The base part 9 is the holding element of the device 1 for accurate positioning of the device 1 independently from fastening at the heart 2, lungs, or the great vessels over the heart 2 and above all over the base of the heart 19. Fastening of the device 1 is thus possible independently from movement excursions performed by the organs of the thoracic cavity, above all independently from heart movements, whereby the apex of the heart 8 moves during contraction in the direction of the base of the heart 19 and thus performs a rotation of approximately 23°. Moreover, the base part 9 is conformable so that it adopts the arching of the inner thorax wall when the suction cups 20 are aspirated and fixed against the thorax.

On the side of the base part 9 facing the heart 2, an application layer 22 may be applied, which comprises a net-like system of small channels with pore-like orifices 23. Via the application layer 22 a lubricating liquid may be distributed on the side of the base part 9 facing the heart 2 in order to reduce sliding friction between the base part 9 and the heart 2 in the functional state of the device 1. The application layer 22 is represented in a top view in FIG. 14a and in a perspective view obliquely from above in FIG. 14b.

In the functional state of the sheathing part 3, the base part 9 extends towards the heart axis X from an upper edge 24 of the sheathing part 3 over the base of the heart 19 down into the region of the apex of the heart 8. This is represented in FIGS. 1 to 3. As apparent from FIG. 1, the upper edge 25 of the base part 9 projects from the upper edge 24 of the sheathing part 3, thereby simplifying coupling of a positioning device 52. This will be discussed later.

Figure 6:
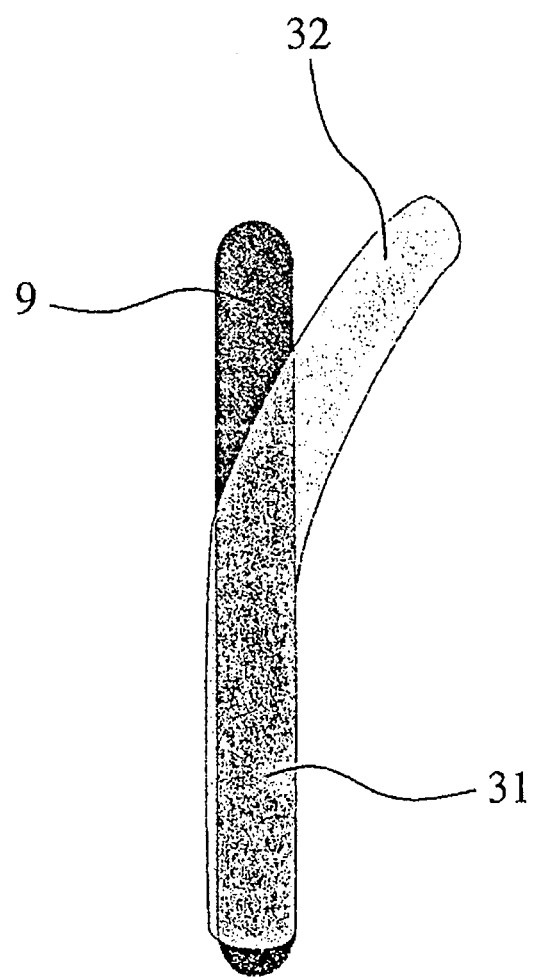
FIG. 6 shows the device represented in FIG. 4 in a lateral view.

As is apparent in particular from FIGS. 3, 4, and 6, the base part 9 in the illustrated embodiment is superficially connected with the sheathing part 3 only between an upper edge region 26 on the side 27 of the base part 9 facing the apex of the heart 8 and a central region 28 of the base part 9, opposite the base of the heart 19 in the functional state of the device 1. Each coiled and/or folded edge portion 11, 12 of the sheathing part 3, extending in the longitudinal direction, comprises in relation to the insertion state shown in FIG. 4 a straight fastening portion 31 for fastening to the base part 9, and a free portion 32 following the straight fastening portion 31, curving away from the plane of the base part 9 and not fastened to the base part 9, with the free portions 32 arranged on both longitudinal sides of the base part 9 converging into a round-bottom-shaped edge portion 13. In relation to the insertion state, the free portions 32 are articulated outwards in the plane of the base part 9 with respect to the straight fastening portions 31. In relation to the insertion state, the sheathing part 3 forms in the region between the fastening portions 31 a recess for receiving and fastening the base part 9. Due to the special shaping of the inflatable edge portions 11, 12, 13, it is ensured that the sheathing part 3 has a small size when it is inserted into the body, thereby permitting a minimally invasive introduction. Moreover, it is ensured that during inflation, sheathing of the heart 2 is performed, starting from front to back over the lateral walls 7 and the apex of the heart 8 up to the region of the posterior walls of the heart 2. Between the free portions 32 a planar region 33 of the sheathing part 3 is provided, which is neither coiled nor folded.

In principle, however, it is of course equally possible for the base part 9 and the sheathing part 3 to be connected together completely over the full length of the base part 9, the base part 9 being adapted to the bulge of the sheathing part 3.

FIG. 5 represents that both longitudinal inflatable edge portions 11, 12 are coiled up from the outside towards the base part 9, and that the layer thickness of the edge portions 11, 12 is substantially constant. Thereby, uniform uncoiling of the edge portions 11, 12 is ensured when converting the inventive device 1 into the functional state. In the direction of the base part 9, the edge portions 11, 12 transition in a trumpet-like fashion into fastening portions 34a comprising fastening surfaces 34. The width of the fastening surfaces 34 corresponds to the width of the longitudinal side surfaces 35 of the base part 9, so that secure fastening of the edge portions 11, 12 to the base part 9 is possible.

In the illustrated embodiment, the edge portions 11, 12 are separated from each other in the region of the straight fastening portions 31 by the base part 9 and are not directly connected together. In principle, however, the edge portions 11, 12 may also be connected directly together in this region of the sheathing part 3, whereby the base part 9 may be placed from above between the edge portions 11, 12 onto the sheathing part 3 and fastened to the sheathing part 3.

Figure 11:
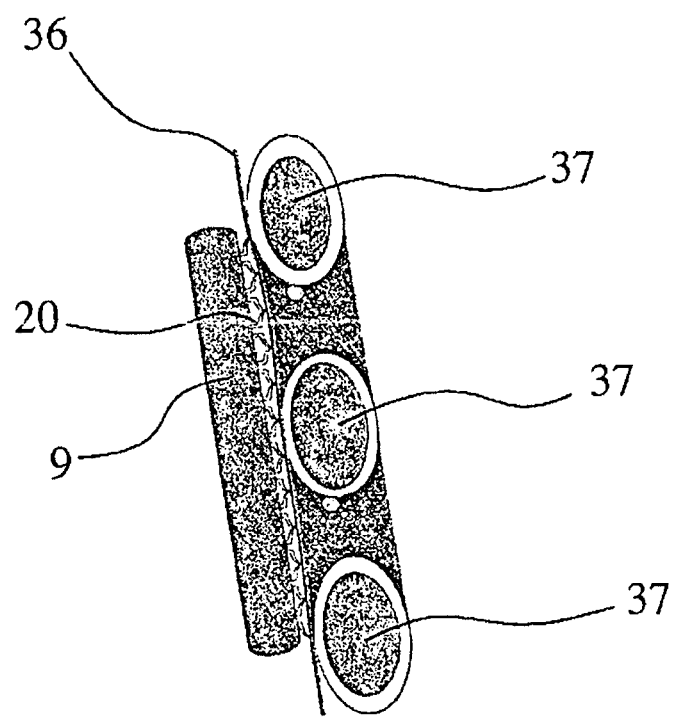
FIG. 11 shows the base part represented in FIG. 9 in a schematic representation in the state aspirated against an inner wall of the thorax.

In FIG. 11, the fastening of the base part 9 with the suction cups 20 to an inner wall 36 of the thorax is represented schematically. Schematically represented ribs 37 extend under the inner wall 36. The sheathing part 3, which is held together with the base part 9 against the inner wall 36, is not represented.

The sheathing part 3 extends, starting from the upper edge 25 of the base part 9, beyond the lower edge 38 of the base part 9 towards the apex of the heart 8. During the operation of insertion or in the insertion state the sheathing part 3 is coiled up (see, FIG. 4). Once the device 1 has been inserted or placed inside the thoracic cavity, the sheathing part 3 is uncoiled in the edge region and thereby encompasses the heart 2 (see, FIG. 1).

Figure 7:
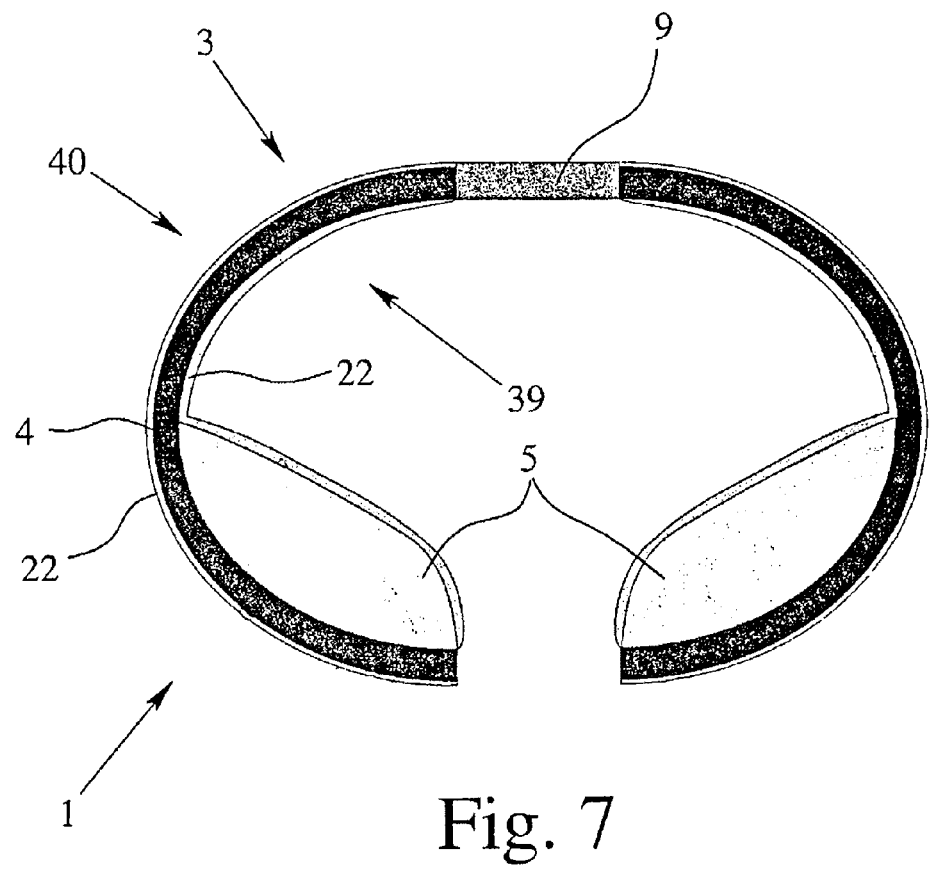
FIG. 7 shows the device represented in FIG. 1 in a cross-sectional view in the functional state of the sheathing part.
Figure 8:
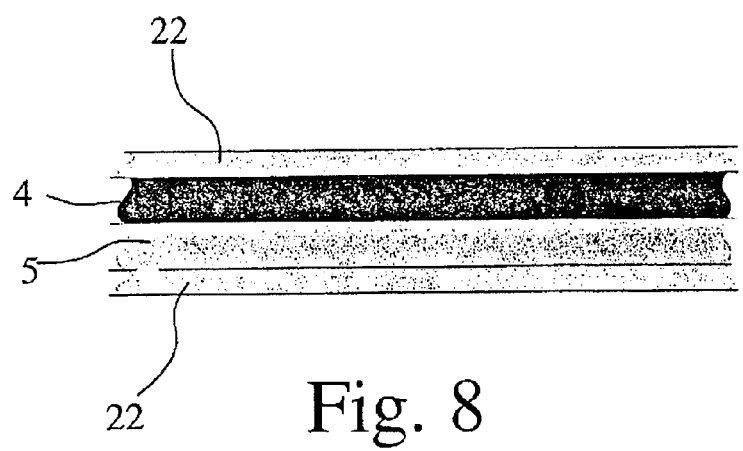
FIG. 8 shows a schematic representation of the layer structure of the sheathing part of the device represented in FIG. 1 in the deflated insertion state of the sheathing part.
Figure 9:
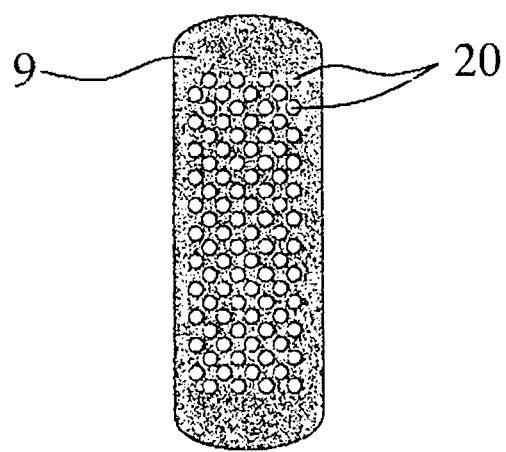
FIG. 9 shows a plan view on a base part of the device represented in FIG. 1.
Figure 10:
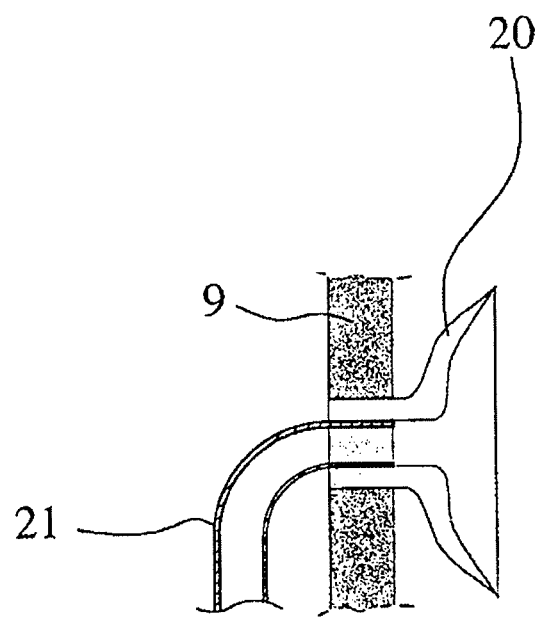
FIG. 10 shows a schematic representation of a suction cup on the base part represented in FIG. 9 for fastening the base part to an inner wall of the thorax.
Figure 14A:
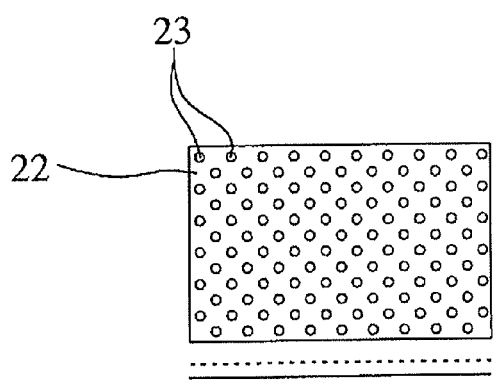
FIGS. 14a & 14b show, respectively, a plan view and a perspective view of an application layer of the device represented in FIG. 1 for application of a lubricating liquid.
Figure 14B:
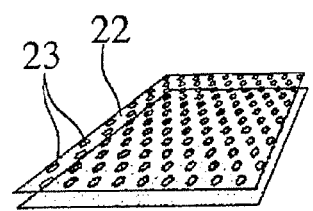

With reference to FIGS. 7 and 8 as well as 12 and 13, the structure of the sheathing part 3 will now be described more in detail. In FIG. 7, a cross-sectional view of the device 1 in the functional state is represented. The sheathing part 3 has a multilayer structure formed of inner and outer application layers 22, which are represented in FIGS. 14a and 14b. The application layers 22 extend on the inner side 39 and on the outer side 40 of the device 1 over the whole surface of the sheathing part 3. The application layers 22 are configured as an inner or outer border layer of the sheathing part 3 and comprise a net-like system of small channels with pore-like orifices 23 towards the inner side 39 and outer side 40 of the sheathing part 3. The small channel system is fed via inlet and outlet lines. For this purpose, one or more pressure-resistant, gas and liquid-tight fluid lines 41 are provided, which are configured for servicing the application layers 22 of the functional part 3 and possibly of the base part 9.

Thus, it is possible to let liquids, gels, gas, or gas mixtures into and out of the net-like small channel system. Due to the application of liquids or gels via the small channel systems on the inner and/or outer surface of the sheathing part 3, the latter is wetted accordingly, a liquid film is created between the surfaces of the sheathing part 3 of the device 1 and the adjacent organs or tissue structures (inside: heart; outside: lungs). Thus, a direct contact fit between the surfaces of the device 1, above all with the heart 2 and the lungs, is avoided.

Figure 13:
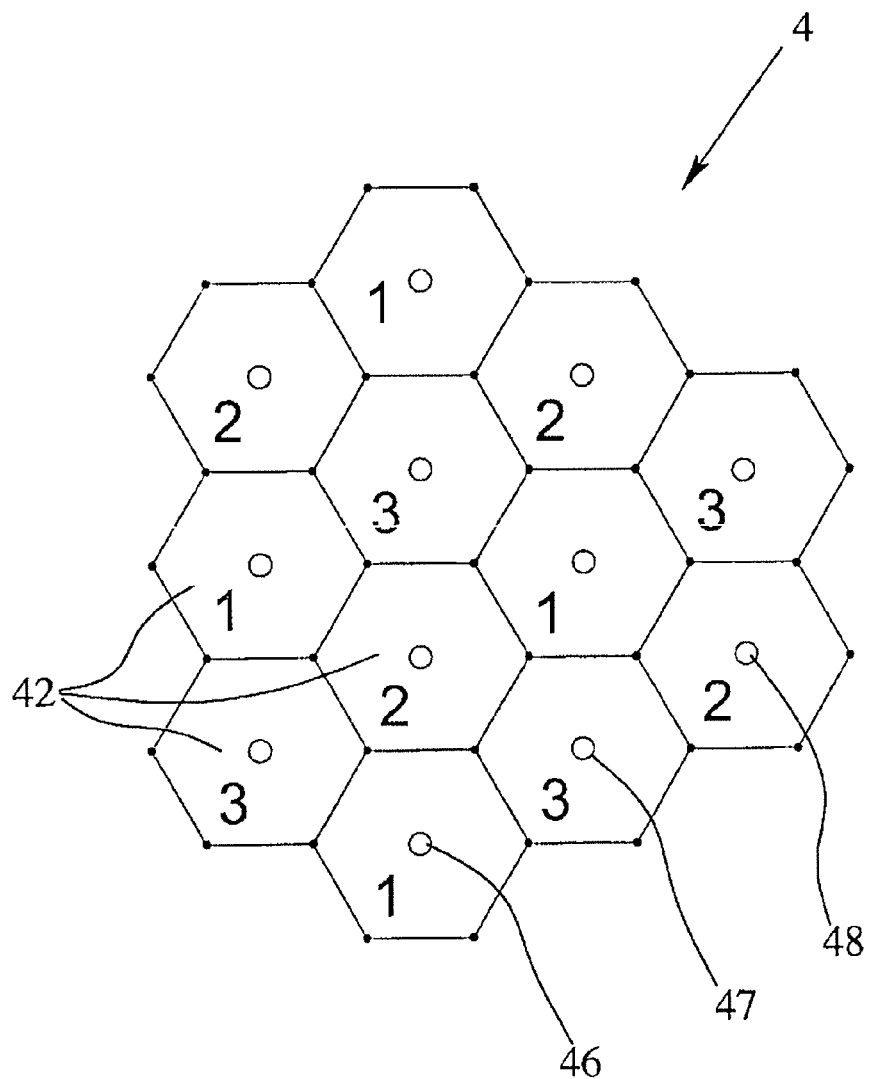
FIG. 13 shows a schematic representation of the stabilization layer represented in FIG. 12 having a honeycomb-like structure.

Moreover, the sheathing part 3 comprises one or more stabilization layers 4. The stabilization layer 4 has a honeycomb structure with a plurality of adjacent inflatable honeycomb cells 42, with the honeycomb cells 42 being connected via fluid lines 43 for cyclically supplying a fluid into the honeycomb cells 42. The fluid lines 43 are very high pressure-resistant, gas and liquid-tight. The honeycomb-like structure of the stabilization layer 4 is represented in FIG. 13. The honeycomb cells 42 have a cross-section tapering towards the heart 2 with a larger base area on the side away from the heart and with a smaller base area on the side close to the heart, so that when a fluid is supplied into the honeycomb cells 42, the honeycomb cells 42 deflate and an inward arching of the sheathing part 3 is caused. It is not represented that, in principle, it is equally possible to provide several stabilization layers 4 overlapping each other in certain sections. The stabilization layer 4 also extends over the whole surface of the sheathing part 3. It is formed of materials which are hardly or not at all extensible and flexible.

Figure 12:
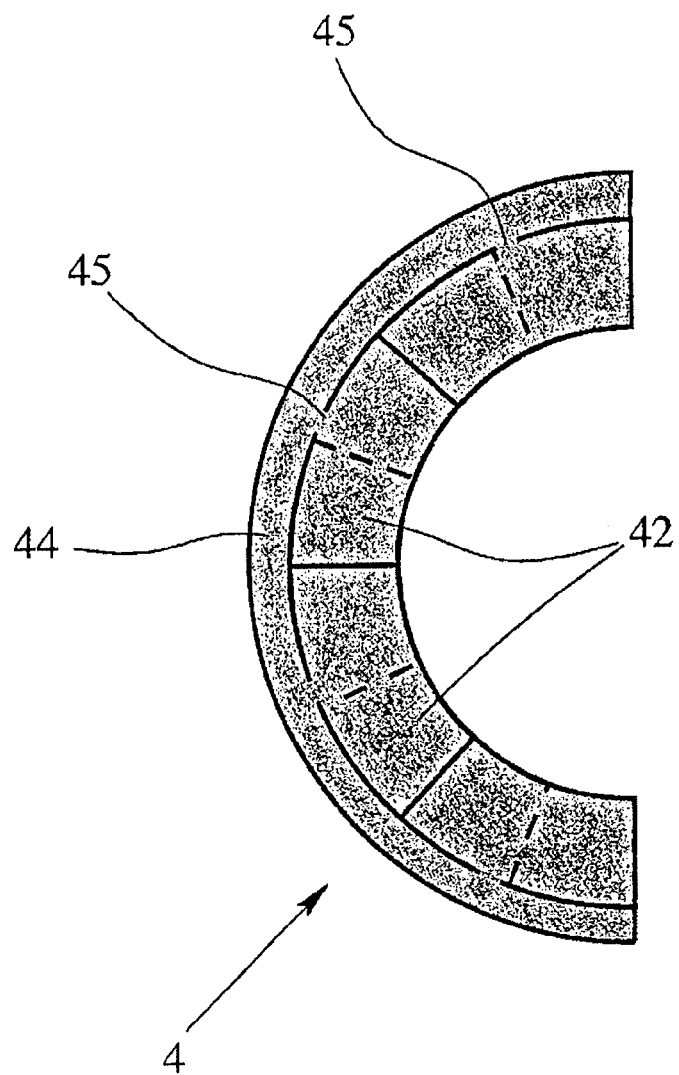
FIG. 12 shows a schematic cross-sectional view of a stabilization layer of the sheathing part of the device represented in FIG. 1 in the functional state of the sheathing part.

As is apparent from FIG. 12, the stabilization layer 4 also has a multilayer structure and comprises, in addition to the honeycomb cells 42, an outer service layer 44 having inlet or outlet lines, through which gases, gas mixtures, or liquids may be supplied into the honeycomb cells 42 or evacuated from the honeycomb cells 42. For this purpose, in the service layer 44, orifices 45 are provided which allow for fluids from the service layer 44 to transition into the honeycomb cells 42. In the insertion state, the honeycomb cells 42 are collapsed or folded up. When a compressed gas or gas mixture is inserted via the service layer 44 into the hardly or not extensible honeycomb cells 42, the cells are deployed and thereby provide the sheathing part 3 of the device 1 with a shape encompassing the heart 2. Due to the fact that the high pressure in the hardly or not extensible honeycomb system is maintained, the sheathing system receives its stability or required rigidity in the thoracic cavity. For this purpose, the stabilization layer 4 formed of the honeycomb-like cell system and the service layer 44 as well as of the fluid lines 43 is composed of adequately chosen gas and pressure-tight materials which are hardly or not extensible.

In order to service the honeycomb cells 42 with a compressed gas or gaseous mixture, mutually separated accesses 46, 47, 48 are provided in neighboring honeycomb cells 42. Three neighboring honeycomb cells 42 (in FIG. 13 marked by different written numbers 1 to 3) can be filled via different fluid lines 43. Thus, non neighboring honeycomb cells 42 are serviced via a common inlet line. If a leakage were to occur, e.g., in a honeycomb cell 42 of type 1, no directly neighboring honeycomb cell 42 of type 2 or 3 would be affected. The sheathing part 3 of the device 1 may then maintain the rigidity and stability for the device 1 via the honeycomb cells 42 of type 2 and 3.

Finally, the sheathing part 3 of the device 1 comprises at least one augmentation layer 5 extending, in contrast to the application layers 22 and the stabilization layer 4 within the sheathing part 3 only inside the region over the lateral walls 7 and the posterior walls of the ventricles, and unlike the other layers, over the full extension of the sheathing part 3. The augmentation layer 5 is formed of an extensible material. Via one or more fluid lines 49, which are configured to be pressure-resistant, gas and liquid-tight, a gas or gaseous mixture may be cyclically filled into the region between the stabilization layer 4 and the augmentation layer 5, so that the augmentation layer 5 distends as represented in FIG. 7.

Due to the fact that the stabilization layer 4 externally applied to the augmentation layer 5 is hardly or not at all extensible, directional distention of the augmentation layer 5 takes place inwards in the direction of the ventricles. Due to the cyclic pumping and subsequent cyclic distention of the extensible augmentation layer 5 the ventricles are compressed and decompressed accordingly, resulting in assistance of the pumping function of the ventricles like a cardiac massage.

Figure 17:
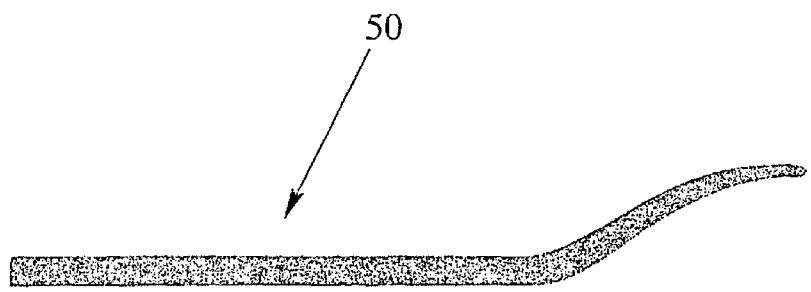
FIG. 17 shows a spatula-shaped probing device.

In FIG. 17, a spatula-shaped auxiliary probing device 50 is represented, which is provided for probing the heart 2, after through a small skin cut of about 3 to 5 cm, an access to the abdominal cavity is created in the region between the xiphoid process of the breast bone and the lower edge of the left coastal arch. The auxiliary probing device 50 is inserted through the opening created in the abdominal cavity, advanced upwards in the direction of the thoracic cavity, going through the Larrey's cleft of the thoracic diaphragm reaching the thoracic cavity, and is further guided from there towards the heart 2. The heart 2 is probed without the front side of the heart 2 being contacted by the auxiliary probing device 50. Thereby, possible adhesions of the pericardium are bluntly detached from the inner thoracic wall.

Figure 18:
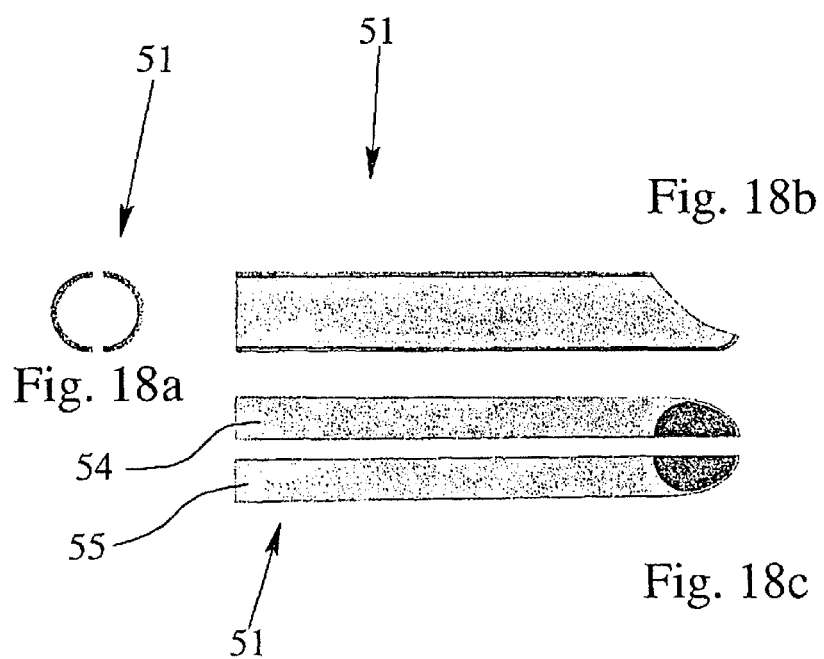
FIGS. 18a-18c show a tubular multipart insertion device for inserting the device represented in FIG. 1 into the thoracic cavity in the insertion state of the sheathing part in a cross-sectional view, a longitudinal sectional view, and a plan view, respectively.

After probing with the auxiliary probing device 50 and removal thereof from the thoracic and abdominal cavity, a tube-like insertion device 51, which is represented in FIGS. 18a to 18c, is guided on the same access path to the heart 2. Once the apex of the heart 8 has been reached, the device 1, by means of a mobile positioning device 52 (FIG. 15), may be advanced through a tube-like insertion channel of the insertion device 51 up to the heart 2. Upon reaching the apex of the heart 8, the insertion device 51 is slightly retracted so as to expose a joint 53 of the positioning device 52 from the proximal end, situated inside the body, of the insertion device 51. Now the device 1 fastened to the joint 53 between the anterior wall of the heart and the inner wall 36 of the thorax may be positioned. Once the device 1 has been positioned, with an orientation towards the heart axis X, the device 1 is fastened to the inner wall 36 of the thorax via the suction device or by means of the suction cups 20 provided at the base part 9. Now, the positioning device 52 may be separated from the base part 9 of the device 1 and extracted through the channel of the insertion device 51 from the inside of the body. Then, the insertion device 51 is removed from the body. Outside the body two mutually releasably connected halves 54, 55 of the insertion device 51 may be separated from each other in order to separate the insertion device 51 from the lines 21, 41, 43, and 49.

Figure 15:
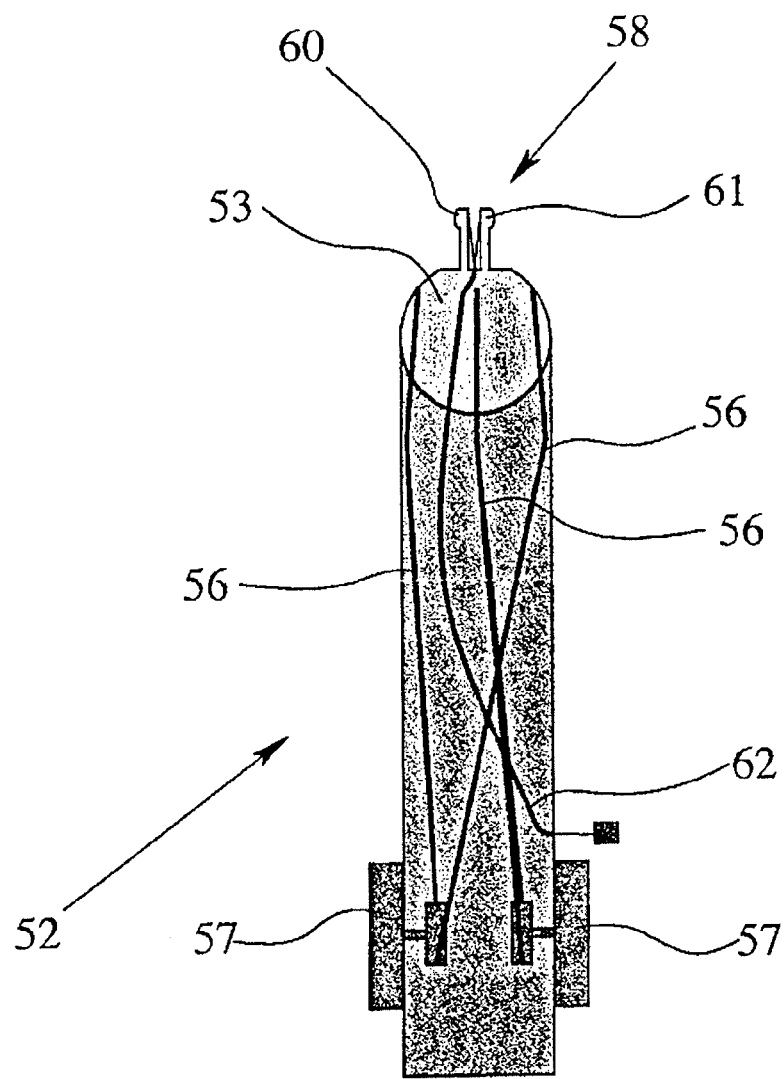
FIG. 15 shows a schematic cross-sectional view of a positioning device for positioning the device represented in FIG. 1.
Figures 16A, 16B:
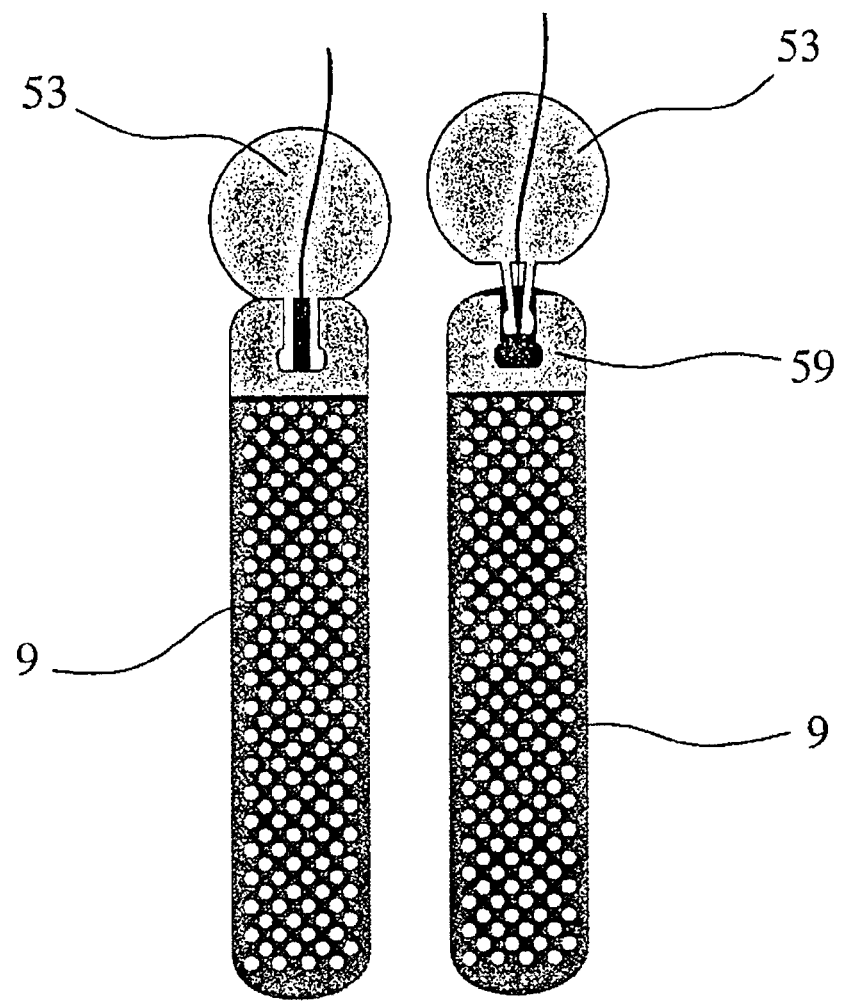
FIGS. 16a & 16b show a head joint of the positioning device represented in FIG. 15, respectively, in the state coupled with the base part represented in FIG. 9 and in the decoupled state.

In FIG. 15, the positioning device 52 is represented in a schematic cross-sectional view. The joint 53 can be turned in the desired direction using wires 56 and adjusting screws 57. At the head of the joint 53, a fastening portion 58 is provided, which may configure a snap-in assembly together with a matchingly configured fastening portion 59 at the base part 9. The fastening portion 59 is provided at the upper edge 25 of the base part 9. This is shown in FIGS. 16a and 16b. The fastening portion 58 comprises two fastening branches 60, 61, which may be pulled together via a control wire 62 in order to release the snap-in assembly formed.

Figure 19:
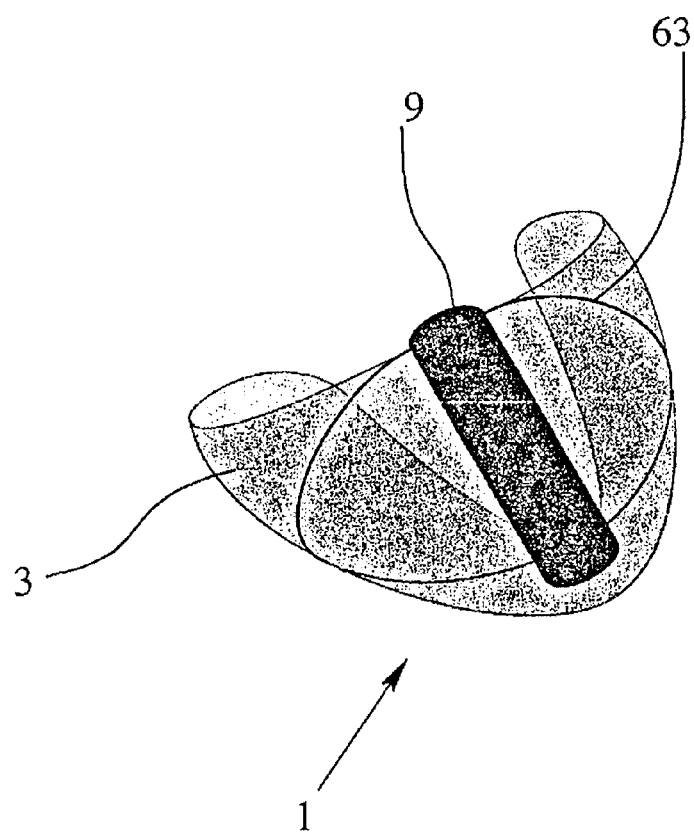
FIG. 19 shows a schematic view of the device represented in FIG. 1 with a stabilization wire for the sheathing part.

FIG. 19 shows that a stabilization wire 63 may be provided for the sheathing part 3, the stabilization wire 63 being arranged extending between the stabilization layer 4 and the augmentation layer 5.

Figure 20:
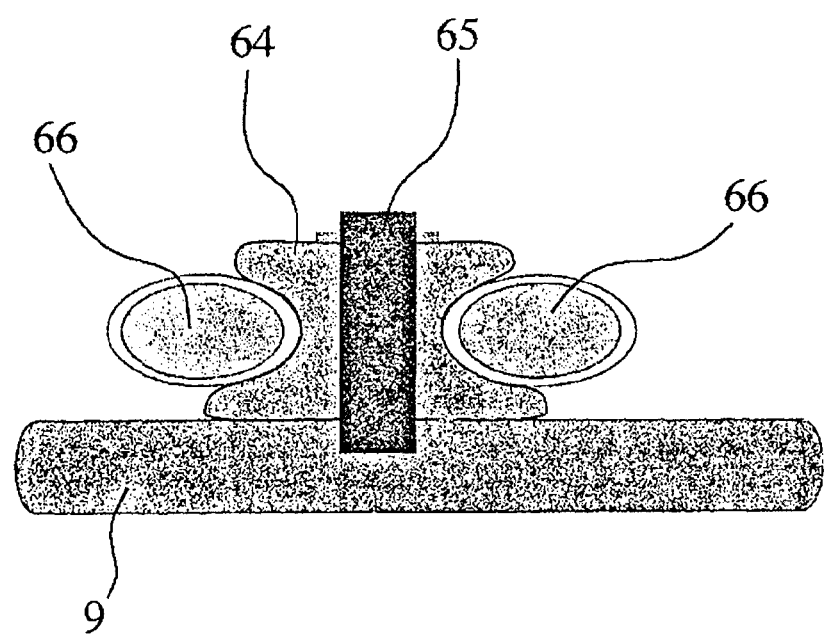
FIG. 20 shows a schematic representation of the fixation of the base part represented in FIG. 9 to the ribs of the thorax.

FIG. 20 represents that the base part 9, and thus, the device 1, can also be fastened to the ribs 66 of the thorax using a gelpack 64 with a fastening element 65.

What is claimed is:

1. A device for at least assisting in pumping of a patient's heart, comprising:
    a multilayer sheathing part configured for compressing a patient's heart at least in certain sections, the sheathing part having at least one stabilization layer for shaping the sheathing part and at least one inner extensible augmentation layer, at least one cavity being formed between the at least one stabilization layer and the augmentation layer, the cavity being expandable and contractible by a fluid for the cyclic compression of the heart, the sheathing part having a coiled insertion state for insertion of the device into a body and an arched functional state adapted for at least partially sheathing or encompassing a patient's heart in use, and means for directing fluid into the stabilization layer for inflating the stabilization layer, at least in certain sections, for converting the sheathing part from the coiled insertion state into the arched functional state, wherein the sheathing part, in the insertion state, comprises two coiled inflatable edge portions extending in a longitudinal direction, wherein a base part is arranged on the sheathing part between the edge portions, wherein the edge portions converge into a common inflatable round-bottom-shaped edge portion that is adapted for sheathing or encompassing an apex of a patient's heart in use, and wherein the at least one stabilization layer has a honeycomb structure with a plurality of adjacent honeycomb cells, wherein the honeycomb cells are connected to at least one fluid line for cyclically supplying a fluid into the honeycomb cells, wherein, the honeycomb cells, in the functional state, have a cross-section tapering towards the heart with a larger base area on a side away from the heart and with a smaller base area on the a close to the heart, and wherein the honeycomb cells are inflatable so as to produce an inward arching of the sheathing part by supplying of fluid into the honeycomb cells.

2. The device according to claim 1, wherein the sheathing part, in the functional state, has a flared tulip shape adapted to the shape of the heart so that, in use, the heart will be sheathed and encompassed from front to back over lateral walls of the heart.

3. The device according to claim 1, wherein the augmentation layer is configured so that, in the functional state, in use, it will be located only in a region above lateral walls and the posterior walls of the heart.

4. The device according to claim 1, wherein the sheathing part, in the insertion state, has an inflatable edge portion which is at least one of spirally coiled and folded from outside to inside.

5. The device according to claim 1, wherein the sheathing part has a hyperbolical recess that is upwardly open for passage of the great heart vessels, the recess being located in the functional state on a backside of the sheathing part for facing the posterior wall of the heart.

6. The device according to claim 1, wherein at least one fastening means for fastening to at least one of an inner wall of the thorax and at least one rib in a manner that is free of at least one of the heart and pericardium.

7. The device according to claim 6, wherein the fastening means comprises at least one suction cup.

8. The device according to claim 7, wherein at least one fluid line connected to the at least one suction cup and opening into an extracorporeal space is provided.

9. The device according to claim 6, wherein said base part is non-inflatable is provided on the front side of the sheathing part in a region of the medial longitudinal axis, wherein the base part comprises the fastening means, and wherein the base part, in the functional state, is adapted to extend in parallel to a heart axis from an upper edge of the sheathing part over the base of the heart down towards the apex of the heart.

10. The device according to claim 9, wherein the base part further comprises at least one outer application layer configured for application of a lubricating liquid on at least one of an inner and an outer side of the base part.

11. The device according to claim 9, wherein the base part is elongated, having a length in the functional state corresponding to about ⅔ of the length of the front side of the sheathing part.

12. The device according to claim 9, wherein the base part is elastic so that the base part, when fastened to an inner wall of the thorax is able to conform to a bulge of the inner wall.

13. The device according to claim 9, wherein the base part, in the functional state, is fastened to the sheathing part only in a region between an upper edge of the sheathing part and a base of the heart.

14. The device according to claim 1, wherein each coiled edge portion comprises a straight fastening portion for fastening to the base part and a free portion following the straight fastening portion on each of opposite longitudinal sides of the base part, the free portion being curved away from a plane of the base part, not being fastened to the base part, and converging into a round-bottom-shaped edge portion.

15. The device according to claim 14, wherein the free portions, in the insertion state, are angled or curved outwards with respect to the straight fastening portions in the plane of the base part.

16. The device according to claim 1, wherein the sheathing part, in the insertion state, comprises a recess for receiving and fastening the base part in a region between the fastening portions.

17. The device according to claim 1, wherein the at least one stabilization layer comprises a plurality of stabilization layers which overlap each other at least in certain sections.

18. The device according to claim 1, wherein the at least one stabilization layer extends over the whole surface of the sheathing part.

19. The device according to claim 1, wherein the sheathing part encompasses the heart in a finger-like fashion in the functional state.

20. The device according to claim 1, wherein at least one stabilization wire is provided, and wherein the stabilization wire is arranged between the at least one stabilization layer and the augmentation layer.

21. The device according to claim 1, wherein at least one service layer is connected to the stabilization layer for supplying a fluid into the honeycomb cells.

22. The device according to claim 1, wherein three fluid lines that are separated from each other are provided, and wherein said honeycomb cells are arranged in separate sets of neighboring cells, each set of neighboring cells being connected to a different one of said fluid lines for filling thereof with fluid.

23. The device according to claim 1, wherein the sheathing part comprises at least one application layer configured for application of a lubricating liquid on at least one of inner and outer sides of the sheathing part.

24. The device according to claim 23, wherein the at least one application layer extends over the whole surface of the sheathing part.

25. The device according to claim 1, wherein the base part comprises at least one fastening portion for releasable fastening with a positioning device.

* * * * *